(12) United States Patent
Enick et al.

(10) Patent No.: US 6,183,815 B1
(45) Date of Patent: Feb. 6, 2001

(54) METHOD AND COMPOSITION FOR SURFACE TREATMENT OF METALS

(75) Inventors: Robert M. Enick, Pittsburgh; Eric Beckman, Aspinwall, both of PA (US)

(73) Assignee: University of Pittsburgh, Pittsburgh, PA (US)

( * ) Notice: Under 35 U.S.C. 154(b), the term of this patent shall be extended for 0 days.

(21) Appl. No.: 09/250,537

(22) Filed: Feb. 16, 1999

Related U.S. Application Data

(63) Continuation-in-part of application No. 08/831,999, filed on Apr. 1, 1997, now Pat. No. 5,872,257, which is a continuation of application No. 08/223,105, filed on Apr. 1, 1994, now Pat. No. 5,641,887.

(51) Int. Cl.[7] .......................................................... B05D 5/00
(52) U.S. Cl. ........................ 427/400; 427/372.2; 427/421
(58) Field of Search ................................... 427/400, 421, 427/372.2

(56) References Cited

U.S. PATENT DOCUMENTS

| | | | |
|---|---|---|---|
| 4,031,038 | 6/1977 | Grinstead et al. | 260/2.2 R |
| 4,171,282 | 10/1979 | Mueller | 252/356 |
| 5,246,507 | 9/1993 | Kodama et al. | 148/250 |
| 5,728,431 | 3/1998 | Bergbreiter et al. | 427/388.1 |
| 5,897,918 * | 4/1999 | Singh et al. | 427/352 |

OTHER PUBLICATIONS

Schonherr et al., Lattice Orientation and Tribology of SAMs of Fluorinated Thiols and Disulfides on Au(111) by AFM: The Influence of the Molecular Structure, Polymer Preprints, pp. 904–905, Aug. 1998.*

Schonherr et al., Self–Assembled Monolayers of Symmetrical and Mixed Alkyl Fluoroalkyl Disulfides on Gold. 1. Synthesis of Disulfides and Investigation of Monolayer Properties, Langmuir, pp. 3891–3897, Feb. 1996.*

Tsao et al., Studies of Molecular Orientation and Order in Self–Assembled Semifluorinated n–Alkanethiols: Single and Dual Component Mixtures, Langmuir, pp. 4317–4322, Jun. 1997.*

Castner et al., X–ray Photoelectron Spectroscopy Sulfur 2p Study of Organic Thiol and Disulfide Binding Interactions with Gold Surfaces, Langmuir, 5083–5086, May 1996.*

* cited by examiner

*Primary Examiner*—Shrive Beck
*Assistant Examiner*—Jennifer Calcagni
(74) *Attorney, Agent, or Firm*—Conley, Rose & Tayon, P.C

(57) ABSTRACT

A method for coating a metal surface, comprising: applying a solution comprising an amide thiol compound and a solvent to a metal surface, allowing the thiol compound to self assemble on the surface, and removing excess thiol compound from the surface. The amide thiol compound is preferably a fluoroalkyl amide thiol and more preferably one having the general formula $F(CF_2)_nCONH(CH_2)_mSH$, where n and m are each 2–20. The solution can be sprayed onto the metal surface, or the metal surface can be dipped into the solution. The surface should be kept wet for a time period sufficient to allow the thiol molecules to self assemble on the metal surface.

12 Claims, No Drawings

METHOD AND COMPOSITION FOR SURFACE TREATMENT OF METALS

CROSS-REFERENCE TO RELATED APPLICATIONS

This application is a continuation-in-part of copending application Ser. No. 08/831,999 filed on Apr. 1, 1997, now U.S. Pat. No. 5,872,257, which is a continuation of Ser. No. 08/223,105 filed Apr. 1, 1994, now U.S. Pat. No. 5,641,887.

STATEMENT REGARDING FEDERALLY SPONSORED RESEARCH OR DEVELOPMENT

Not Applicable.

FIELD OF THE INVENTION

The present invention relates to a process for forming a self-assembled layer on a metal surface. Still more particularly, the present invention relates to a method for coating a thiol-containing solution onto a treated metal substrate. The thiol has been designed to not have the stench characteristic of conventional thiols, the methods of application employ benign chemicals and simple techniques, and the treated metal surfaces feature improved corrosion resistance even though the layer is invisible.

BACKGROUND OF THE INVENTION

There are many instances where it is desirable to protect the surface of a metal from exposure to air or water in the environment. In particular, it is often desirable to minimize the exposure of the metal surface to moisture, oxygen, sulfur-containing gases and other reactive molecules that may be present in the air. One simple way to achieve this goal is to encapsulate the metal object in a polymeric container. In the case of rare coins, encapsulation of the coin and a small gap of air surrounding the coin in airtight plastic case is referred to as "slabbing." Alternately, the metal object itself can be coated with a wax or polymer in solution, such an acrylic polymer lacquer, that contacts and covers the coin with a relatively thick, transparent layer. This layer is obvious to the naked eye, changes the appearance or sheen of the metal, and is subject to yellowing, cracking and peeling as the polymer ages. When the object is large, slabbing or encapsulation of the metal object in an airtight plastic container is not practical. Aesthetic or other considerations may preclude coating the metal with a layer of polymer. Therefore, alternative methods of protection are desired.

The coating of a metal surface by self assembly of organic molecules has been reported in the literature. The process yields a well defined surface that moderates and mediates the chemistry of the underlying metal. By self assembled, it is meant that the molecules in the coating layer each attach one of their ends to the surface, and then "assemble" in a uniform geometric pattern on the metal, thereby aligning themselves consistently and uniformly and forming a layer whose thickness is approximately equal to the length of one molecule.

For example, the self assembly of thiol compounds, i.e. those having the general formula $H(CH_2)_nSH$, on metals like gold, silver or copper is known in the art. In the self assembled layer, the sulfur atoms are bound to the metal surface and the alkyl tails are pointed away from the metal surface. This outermost layer of hydrocarbons tends to make the surface of the layer at least slightly hydrophobic. A severe disadvantage to these alkyl thiol metal surface treatments, however, is that the thiol compounds tend to have prohibitively unpleasant odors. Although alkyl thiols having higher molecular weights are less odiferous, they exhibit reduced solubility in most practical solvents.

Hence, it is desired to provide a self-assembling metal surface treatment that produces a gas-, water-, oil- and corrosion-resistant outer layer without producing an undesirable odor during the application of the layer, and without employing hazardous chemical solvents. It is further desired to provide a metal surface treatment that is a simple and easy to apply and relatively inexpensive.

SUMMARY OF THE INVENTION

The present invention provides a self-assembling metal surface treatment that produces a gas-, water-, oil- and corrosion-resistant outer layer. The present metal surface treatment is simple and easy to apply and relatively inexpensive. According to a preferred embodiment, a solution of a fluoroalkylamide thiol in a light alcohol is applied to the metal surface that is to be protected and maintained in a wet state for a predetermined amount of time, which serves to allow the thiol molecules to self-assemble into a monolayer on the metal surface. One way to accomplish the self-assembly period is to spray a thin layer of the thiol solution onto the metal surface and then allow it to dry undisturbed. An alternative technique consists of dipping the metal into the thiol solution and allowing it to remain in the solution for a predetermined self-assembly period before removing it from the solution and drying it.

In alternative embodiments, the fluoroalkylamide thiol is replaced with alkyl amide thiols to lower the cost of the thiol. Similarly, the light alcohol solvent can be replaced with a hydrofluoroether or a fluoroalkane if a non-flammable solution is desired, although the integrity of the self-assembled layer is decreased. In any case, the thiol monolayer is kept in wet contact with the metal surface as the thiol self-assembles in a monolayer during the evaporation of the solvent. Excess coating material (thiol) is removed by rinsing and/or polishing, and the surface is dried.

DETAILED DESCRIPTION OF A PREFERRED EMBODIMENT

According to the present invention, a coating solution comprising an alkylamide thiol dissolved in a low molecular weight alcohol is applied to the metal surface that is to receive the protective layer. Details of these steps and compositions are as follows.

Thiols

In a preferred embodiment, the thiol compounds used to form a protective layer on the metal surface comprise fluoralkyl amide thiols having the general formula $F(CF_2)_n(CH_2)_pCONH(CH_2)_mSH$, where n, m and p can each be 0–20. It is preferred that n be 1–20. $F(CF_2)_n$ is the fluoroalkyl section of the molecule and is outermost when the protective layer self-assembles. Hence, it provides a fluorinated outer surface that provides the tarnish resistance. The CONH group is the amide section, which provides hydrogen-bonding between the thiols, and SH is the thiol head group that chemisorbs to the metal/tarnished metal surface. A particularly preferred embodiment of the present coating compound is $F(CF_2)_6CONH(CH_2)_2SH$. It is believed that the integrity of the layer formed by these compounds is enhanced by the action of van der Waals forces between the coating molecules and by hydrogen bonding between thiols at the amide group.

An alternative to the use of fluoralkyl amide thiols comprises alkyl amide thiols with the general formula $H(CH_2)_nCONH(CH_2)_mSH$, where n and m are each 1–20. It is expected that these compounds will be less expensive than the fluoralkyl amide thiols. The alkyl amide thiols may still be free of odor because the hydrogen bonding group lowers the vapor pressure of the neat thiol. Although the protective layer formed by alkyl amide thiols on the surface of the metal will not have a fluorinated characteristic, it comprises hydrocarbons and so is expected to repel water to some extent. Nevertheless the fluorinated compounds are presently preferred, as fluorinated coatings are more water repellant and are also oil repellant.

An outstanding characteristic of the present thiols is their lack of any detectable odor. The unpleasant and dangerous stench associated with conventional alkylthiols is the primary reason that they have not been used more extensively. Although several commercial silver tarnish-inhibiting products contain alkylthiols, their strong stench is readily detected when the products are used.

Solvent

The preferred solvent should be one that is safe, easy to handle, and inexpensive, as well as one that dissolves the self-assembling compound. One suitable class of solvents is the hydrofluoroethers or fluoroalkanes. These are nonflammable, and are effective solvents for the desired compounds. A disadvantage of the hydrofluoroethers and fluoroalkanes is that they are relatively expensive, and the integrity of the self-assembled layer is inferior to that observed in other solvents.

Preferred solvents therefore are light alcohols or alcohol water mixtures. By light alcohols are meant alcohols having six or less carbon atoms. For example, alcohols such as isopropyl alcohol, normal propanol or mixtures of either propanol with small amounts (30 vol % or less) of water have been found to be effective solvents for this application. They display sufficient solvent strength to dissolve the requisite amounts of the thiol, they evaporate slowly enough to provide the thiols with an opportunity to self assemble, and they are not such strong solvents that the self assemble period is unduly increased by the tendency of the thiols to remain in the solvent.

2-butoxyethanol (six carbons and an oxygen ether link) is a common alcohol found in household window cleaning products. The this alcohol dissolves the thiol, its boiling point is very high and vapor pressure low, providing a long time for the metal to remain wet and give the thiols an opportunity to self assemble. The self assembled layers formed with this solvent are relatively poor, however. This solvent is so strong that the thiols do not chemisorb onto the metal surface rapidly; the strong interactions between the 2-butoxyethanol and the thiol hinder the chemisorption of the thiols to the metal.

Because the preferred solvents, propanol and propanol/water mixtures are volatile and relatively harmless ("rubbing alcohol" is a mixture of isopropanol and water), they can readily be evaporated from a thin film on the metal surface. These solvents are particularly suitable for use in the preferred spraying and drying technique. If the solvent is too volatile, it will evaporate before the thiols have time to self assemble. The self assembly period depends in part on the concentration of thiol in the solution, but in general it is preferred that the solvent be such that a sprayed-on layer does not fully evaporate in less than several seconds.

In alternative embodiment, liquid carbon dioxide can be used as the solvent. In this case, the coating process would have to be carried out under pressure, so as to avoid rapid evaporation of the $CO_2$ solvent. On the other hand, use of liquid $CO_2$ as a solvent has the advantage of allowing rapid drying of the surface (by depressurization) once the desired self assembly period has elapsed. Liquid $CO_2$ has the further advantage of being non-toxic, non-flammable, and environmentally safe.

Process

A preferred spray-formulation comprises between about 0.1 and about 5.0 wt % thiol, and more preferably between about 0.1 and about 1.0 wt % thiol, with the balance being solvent. If the thiol concentration is too low, there will not be a strong enough driving force for the thiols to self-assemble in a reasonable or practical amount of time. If the thiol concentration is too high, the solution will be unnecessarily expensive and may also leave a thick film of excess thiol on the metal, which may be difficult to remove.

The present invention has applicability either for bright metal surfaces that are to be kept clean and tarnish free or for preserving old and/or rare metal surfaces in their current state, even if tarnished. It is necessary to remove any grease, oil or dirt from the surface, however, prior to application of the thiol. In the case of a bright metal surface, any suitable metal cleaning or tarnish removing product or process can be used to remove any oxidation from the surface. The polished surface should be cleaned and dried before application of the thiol coating. In the case of the preservation/conservation of old or rare metal surfaces, it may be acceptable to clean damaged or corroded metal prior to application of the thiol. In other cases, it may be desirable to minimize mechanical damage to the surface, to not remove any tarnish or toning, and to prevent further chemical damage or oxidation. In this case, the surface can be thiol-coated without pretreatment because the thiols are also effective coating agents for metal oxides and sulfides. For example, the application of the thiol to rare coins will typically employ no surface treatment prior to application because such treatments diminish the coin's value.

Once the surface is ready for coating the following steps are preferably carried out. The solution is sprayed onto the surface using a pump sprayer with a mist discharge until the entire metal surface is wet. In order to minimize runoff, it is preferred to place the object in a position such that its surfaces are as horizontal as possible. The surface is left undisturbed for a time sufficient to allow the solvent in the film on the surface to evaporate. The concentration of thiol in the solvent must be high enough for a self-assembled monolayer to form before the solvent evaporates. Depending on the solvent employed, the thiol molecules will require 0.1–10 minutes of wet time to self assemble a coating layer on the metal surface. Therefore, it is preferred that the solvent not evaporate in less than 0.1 minute.

Once the self assembled layer has had time to form, it is necessary to remove the excess thiol from the surface The thin film of liquid sprayed on the surface of the metal contains a great excess of thiol. This high concentration is required to drive the self-assembly of the thiol before the solvent evaporates. The excess thiol deposits in a non-oriented, non-aligned manner on top of the monolayer. It is undesirable to leave excess thiol on top of the self-assembled monolayer, as its unassembled nature causes the surface to be less hydrophobic and its presence can be visible to the naked eye in the form of "rainbows" of color on the surface or brown deposits of very thick layers. The removal of excess thiol can be accomplished by either polishing the metal with a soft cloth and/or by rinsing the metal surface thoroughly with water for 10–30 seconds. When the excess thiol is removed, the water will start to "bead up" on the coated surface, indicating that only the hydrophobic self-assembled monolayer remains on the metal.

Once the excess thiol is removed, the surface can be dried with a cloth or left to dry via evaporation. If the surface is fragile or should not be polished with a cloth (e.g. rare coins), rubbing should be avoided and the coated surface should be allowed to air dry after rinsing.

In an alternative embodiment, the metal object can be immersed in a thiol/solvent mixture. If the metal object is dipped and removed, the principles affecting drying time are as discussed above. Alternatively, the object can be held in the solution for the desired self assembly period. The immersion period depends on the metal substrate and on the concentration of thiol in solution and can range from less than 1 minute for highly concentrated solutions of thiol in solvent to over 2 hours for very dilute solutions of thiol in solvent. It is expected that immersion times on the order of 1 to 5 minutes will be practical and easily achievable. The immersion method has the advantage of carefully controlling the time of exposure of the metal surface to the thiol containing liquid, with the result that shorter times can be used for high thiol concentrations in the solution and longer times can be used for low concentrations. This allows the user to tailor the system as desired. An example of a suitable concentration and immersion time is: 30 minutes in a 1 wt. % fluoroalkylamide solution. After removal from the solution, the object is preferably rinsed with water and dried. It will be understood that the thiol solution of the present invention can be applied to the metal surface by any suitable means, such as by "painting," rolling, or the like, although it is typically preferred to use a less mechanical method (such as spraying) so as to minimize damage to the metal surface.

While it is preferred and easiest to conduct the foregoing coating steps at room temperature and in air, both the temperature and the atmosphere can be varied slightly without affecting the quality of the monolayer. For example, the time period required for self assembly can be reduced by elevating the temperature of the solution slightly. Warming the solution will also increase the evaporation rate and will thus reduce the wet time available for self assembly. In some instances, it may be desirable to polish the metal surface and apply the coating in an oxygen-free environment, such as under a nitrogen blanket, so as to minimize the amount of oxidation that occurs before completion of the monolayer.

While the present invention provides an effective method for providing a tarnish resistant coating on many metals, including but not limited to gold, silver, nickel, copper, brass, tin, iron and the like, it is not effective for aluminum, aluminum oxide-coated aluminum or aluminum alloys. The coating is also effective at protecting "toned" or "tarnished" metal surfaces if it is desirable to conserve this state of the metal (e.g. rare coins). The present coating can be applied instead of other types of protection, including slabbing and polymer coating, or can be used in conjunction with slabbing. For example, the present thiol coating can advantageously be applied to coins that are to be slabbed, especially copper-based alloys that are known to continue to "tone" or tarnish even after they are encapsulated.

EXAMPLE 1

A solution comprising 1.0 wt. % of F(CF2)6CONH(CH2)2SH (tridecafluorohexyl amide ethylthiol) in 99.0 wt. % aqueous isopropyl alcohol is sprayed onto a silver surface. The thiol has no detectable odor before of after dissolution in the alcohol. The alcohol comprises 91 vol. % isopropyl alcohol and 9 vol. % water. The surface dries in several minutes, and is then rinsed and dried with a soft cloth. The surface is coated with a monolayer that is hydrophobic, is not detectable to the naked eye, and is not readily removed by rubbing. When exposed to a "tarnish chamber" that provides a very corrosive environment (high $SO_2$ concentration) for silver, the coated surface did not tarnish, while a similar metal surface that was not coated tarnished severely. The coating does not discolor, crack or peel. Surface analysis indicates that a uniform, self-assembled monolayer has been established on the silver.

EXAMPLE 2

A solution comprising 1.0 wt. % of F(CF2)6CONH(CH2)2SH (tridecafluorohexyl amide ethylthiol) in 99.0 wt. % isopropyl alcohol is sprayed onto a silver surface. The thiol has no detectable odor before of after dissolution in the alcohol. The alcohol comprises 100 vol. % isopropyl alcohol. The surface dries in several minutes, and is then rinsed and dried with a soft cloth. The surface is coated with a monolayer that is hydrophobic, is not detectable to the naked eye, and is not readily removed by rubbing. When exposed to a high $SO_2$ concentration, the coated surface did not tarnish, while a similar metal surface that was not coated tarnished severely. The coating does not discolor, crack or peel. Surface analysis indicates that a uniform, self-assembled monolayer has been established on the silver.

EXAMPLE 3

A solution comprising 1.0 wt. % of F(CF2)6CONH(CH2)2SH (tridecafluorohexyl amide ethylthiol) in 99.0 wt. % normal propanol is sprayed onto a silver surface. The thiol has no detectable odor before of after dissolution in the alcohol. The alcohol comprises 100 vol. % normal propanol. The surface dries in several minutes, and is then rinsed and dried with a soft cloth. The surface is coated with a monolayer that is hydrophobic, is not detectable to the naked eye, and is not readily removed by rubbing. When exposed to a high $SO_2$ concentration, the coated surface did not tarnish, while a similar metal surface that was not coated tarnished severely. The coating does not discolor, crack or peel. Surface analysis indicates that a uniform, self-assembled monolayer has been established on the silver.

EXAMPLE 4

A solution comprising 1.0 wt. % of F(CF2)6CONH(CH2)2SH (tridecafluorohexyl amide ethylthiol) in 99.0 wt. % normal propanol is sprayed onto pennies and silver dollars. The thiol has no detectable odor before of after dissolution in the alcohol. The coins are not polished or cleaned prior to treatment. Some coins are not tarnished, while others have heavy toning. The alcohol comprises 100 vol. % normal propanol. The surface dries in several minutes, and is then rinsed and allowed to dry via evaporation. The metal and tarnished metal surfaces are each coated with a monolayer that is hydrophobic and is not detectable to the naked eye. When exposed to a high $SO_2$ concentration, the coated surface did not tarnish any further, while similar coins that were not coated tarnished severely. The coating does not discolor, crack or peel.

EXAMPLES 5(a)–(h)

Eight solutions were found to give less than desirable results. The solutions and the explanation for their failure to provide satisfactory results are as follows:

(a) 1.0 wt. % of $F(CF_2)_6CONH(CH_2)_2SH$ in 99.0 wt. % 2-butoxyethanol;
(b) 0.1 wt % of $F(CF_2)_6CONH(CH_2)_2SH$ in 99.0 wt. % normal propanol;

(c) 0.1 wt % of $F(CF_2)_6CONH(CH_2)_2SH$ in 99.0 wt. % isopropanol;

(d) 0.1 wt % of $F(CF_2)_6CONH(CH_2)_2SH$ in 99.0 wt. % (91 vol. % isopropanol, 9 vol. % water);

(e) 1.0 wt % of $F(CF_2)_6CONH(CH_2)_2SH$ in 99.0 wt % 3M hydrofluoroether HFE-7100, $C_4F_9OCH_3$;

(f) 1.0 wt % of $F(CF_2)_6CONH(CH_2)_2SH$ in 99.0 wt % 3M hydrofluoroether HFE-7200, $C_4F_9OC_2H_5$;

(g) 0.5 wt % fluoroalkylamidethiol in 99.5 wt % 1-propanol; and (h) 0.5 wt % fluoroalkylamidethiol in 99.5 wt % (91 vol % isopropanol, 9 vol % water).

Each of the foregoing solutions were sprayed onto a silver surface. The surface was allowed to dry, and was then rinsed and dried with a soft cloth. In each case, the surface was poorly coated with a monolayer that was hydrophobic, not detectable to the naked eye, and not readily removed by rubbing. Surface analysis results indicated that this layer did not uniformly cover the entire silver surface, although it provided some tarnish resistance when the silver was exposed to the corrosive environment. It is believed that the hydrofluoroethers were too volatile, the 2-butoxyethanol was too strong a solvent, and 0.1 wt % was too low a concentration for the spray application. Results of the 0.5 wt % solutions were comparable to or better than the 0.1 wt % solutions of the fluoroalkylamidethiol in the same solvents, but the monolayer coverage was significantly less than that achieved in the 1 wt % solutions.

Crosslinkable fluorinated thiols

Crosslinkable fluorinated thiols are also contemplated for this application. Unlike the fluoroalkylamidethiols, which can hydrogen-bond to one another, these crosslinkable fluorothiols are covalently bonded into a macromolecular sheet across the surface of the silver. This is expected to enhance the longevity and mechanical integrity of the coating. The crosslinking occurs between the thiol headgroup and the fluorinated tail, and is accomplished via UV radiation. These compounds tend to be much more expensive than the fluoroalkylamide thiols, however.

While the present fluid composition has been described according to a preferred embodiment, it will be understood that departures can be made from some aspects of the foregoing description without departing from the essence of the invention. For example, the thiol compound and solvent can each be varied and the application environment can be varied, so long as an odorless, self assembled thiol monolayer is formed on a metal surface.

What is claimed is:

1. A method for providing a gas-, water-, oil- and corrosion-resistant coating on a metal surface, comprising:

(a) applying a solution comprising fluoroalkyl amide thiol compound dissolved in a liquid solvent to a metal surface;

(b) allowing the thiol compound to self assemble on the surface; and (c) removing excess thiol compound from the surface;

wherein steps (a) and (b) are carried out at substantially ambient temperature and step (b) is completed in less than 30 minutes.

2. The method according to claim 1 wherein the amide thiol compound is a fluoroalkyl amide thiol having the general formula $F(CF_2)_nCONH(CH_2)_mSH$, where n and m are each 2–20.

3. The method according to claim 1 wherein the amide thiol compound comprises $F(CF_2)_6CONH(CH_2)_2SH$.

4. The method according to claim 1 wherein the solvent is selected from the group consisting of hydrofluoroethers, fluoroalkanes, light alcohols, mixtures of alcohol and water, and liquid carbon dioxide.

5. The method according to claim 1 wherein the solution is sprayed onto the metal surface and the thiol compound self assembles during evaporation of the solvent.

6. The method according to claim 1 wherein the metal surface is immersed in the solution and held in the solution for a time sufficient to allow the thiol to self assemble on the metal surface.

7. The method according to claim 1 wherein the metal surface is dipped into and removed from the solution and the thiol compound self assembles during evaporation of the solvent.

8. The method according to claim 1 wherein the metal surface is selected from the group consisting of silver, copper, nickel, tin, iron, zinc and alloys thereof and metal oxides and metal sulfides and metal sulfates.

9. The method according to claim 1 wherein the solvent is selected from the group consisting of hydrofluoroethers, fluoroalkanes, and liquid carbon dioxide.

10. The method according to claim 1, further including removing excess thiol from the surface after a coating layer has assembled on the surface.

11. A method for providing an oxidizable metal surface with a corrosion-resistant coating, comprising:

(a) applying a solution comprising an amide thiol compound and a solvent to a metal surface, wherein the solvent is selected from the group consisting of hydrofluoroethers, fluoroalkanes, mixtures of alcohol and water, and liquid carbon dioxide; and (b) allowing the thiol compound to self assemble and form a coating layer on the surface at substantially room temperature in less than about 30 minutes.

12. The method according to claim 11 wherein the metal surface is selected from the group consisting of silver, copper, nickel, tin, iron, zinc and alloys thereof and metal oxides and metal sulfides and metal sulfates.

* * * * *